(12) United States Patent
Finch et al.

(10) Patent No.: US 7,888,637 B2
(45) Date of Patent: Feb. 15, 2011

(54) SAMPLE PREPARATION PLATE FOR MASS SPECTROMETRY

(75) Inventors: Jeffrey W. Finch, Gig Harbor, WA (US); John C. Gebler, Hopkinton, MA (US); Santiago Vazquez, Merewether (AU)

(73) Assignee: Waters Technologies Corporation, Milford, MA (US)

( * ) Notice: Subject to any disclaimer, the term of this patent is extended or adjusted under 35 U.S.C. 154(b) by 172 days.

(21) Appl. No.: 11/829,613

(22) Filed: Jul. 27, 2007

(65) Prior Publication Data

US 2008/0093548 A1 Apr. 24, 2008

Related U.S. Application Data

(63) Continuation of application No. 11/200,583, filed on Aug. 10, 2005, now abandoned, which is a continuation of application No. PCT/US2004/003890, filed on Feb. 10, 2004, application No. 11/829,613, which is a continuation-in-part of application No. 11/196,820, filed on Aug. 3, 2005, now Pat. No. 7,294,831, which is a continuation of application No. 10/223,401, filed on Aug. 19, 2002, now Pat. No. 6,952,011.

(60) Provisional application No. 60/446,236, filed on Feb. 10, 2003.

(30) Foreign Application Priority Data

Aug. 17, 2001 (GB) ................... 0120131.8

(51) Int. Cl.
*H01J 49/42* (2006.01)
*H01J 49/04* (2006.01)
(52) U.S. Cl. .......... 250/288; 250/281; 250/282
(58) Field of Classification Search ............. 250/288
See application file for complete search history.

(56) References Cited

U.S. PATENT DOCUMENTS 6,952,011 B2 * 10/2005 Brown et al. ............. 250/288

* cited by examiner

*Primary Examiner*—David A Vanore
(74) *Attorney, Agent, or Firm*—Siquin Huang; Anthony J. Janiuk; Stephen J. Gauder

(57) ABSTRACT

Disclosed herein is a sample preparation plate used to prepare a sample for mass spectrometry. In particular, a sample plate used to concentrate a sample as well as remove contaminants from the sample while providing easy manipulation of small liquid droplets on a surface with minimal sample loss.

12 Claims, 5 Drawing Sheets

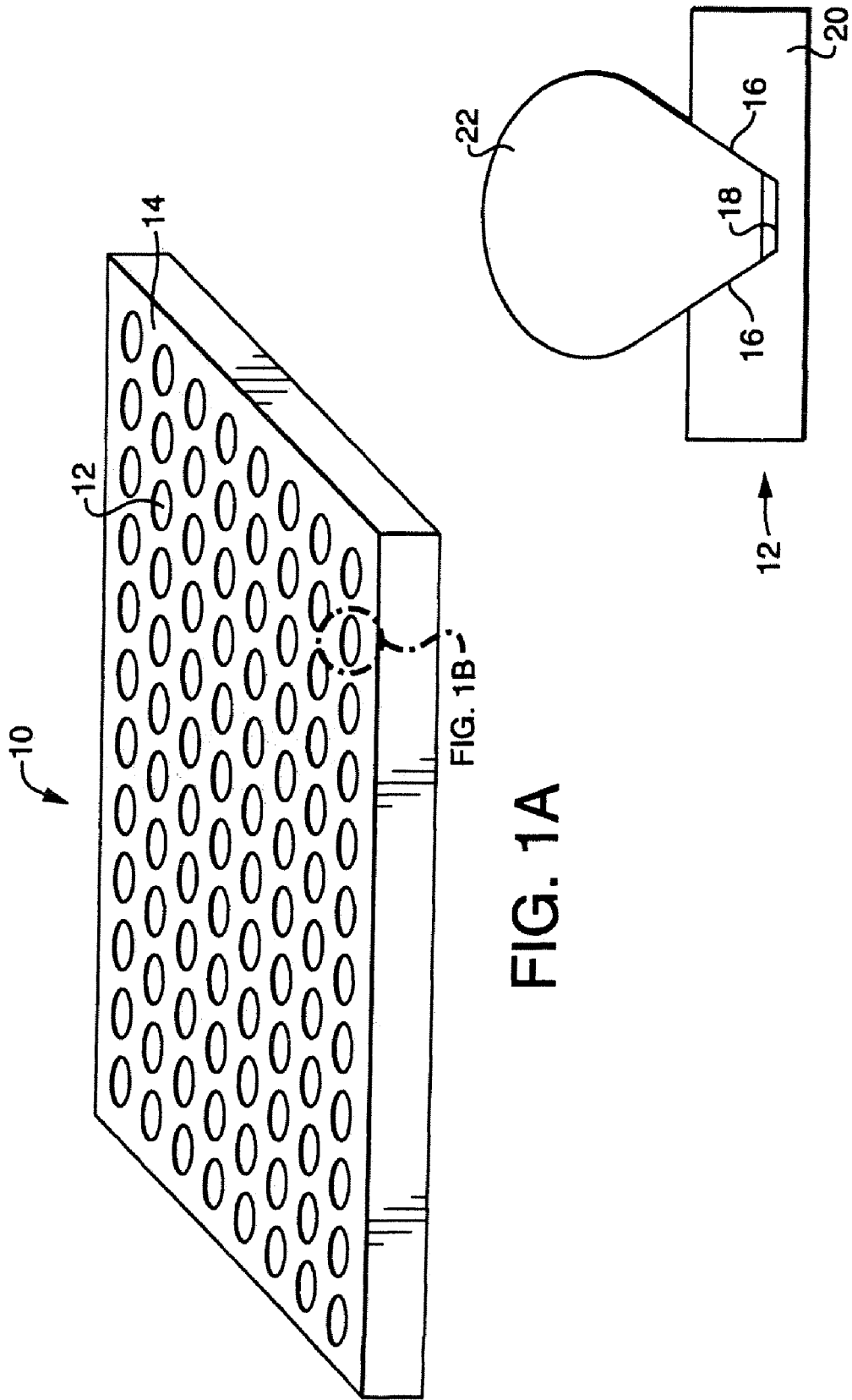

SAMPLE PREPARATION PLATE FOR MASS SPECTROMETRY

CROSS REFERENCE TO RELATED APPLICATIONS

This application is a continuation of U.S. application Ser. No. 11/200,583, filed Aug. 10, 2005, which now abandoned is a continuation of International Application No. PCT/US2004/003890, filed Feb. 10, 2004 and designating the United States, which claims benefit of and priority to U.S. Provisional Application No. 60/446,236, filed Feb. 10, 2003. This application is also a continuation-in-part of U.S. application Ser. No. 11/196,820, filed Aug. 3, 2005, now U.S. Pat. No. 7,294,831 which is a continuation of U.S. application Ser. No. 10/223,401, filed Aug. 19, 2002, now U.S. Pat. No. 6,952,011, issued Oct. 4, 2005, which claims benefit of and foreign priority to United Kingdom Application No. GB 0120131.8, filed Aug. 17, 2001. The contents of all of these applications are which is expressly incorporated herein by reference in their its entirety.

FIELD OF INVENTION

The present invention pertains to a sample preparation plate used to prepare a sample for mass spectrometry. In particular, the instant invention pertains to a sample plate used to concentrate a sample as well as remove contaminants from the sample while providing facile manipulation of small liquid droplets on a surface with minimal loss of sample.

BACKGROUND OF THE INVENTION

Mass spectrometric analysis of analytes such as small molecules as well as large biomolecules like proteins and oligonucleotides often involves sample preparation. It is axiomatic that the cleaner a sample is prior to analysis, then often the better analytical result is obtained.

Currently, sample purification of samples destined for mass spectrometric analysis in low volumes, i.e., <100 µL, prior to introducing the sample into a mass spectrometer, using an ionization technique such as MALDI or static nanospray, is often accomplished employing ZipTips® pipette columns from the Millipore Corporation. Alternatively, microcolumns prepared from gel-loader tips or short sections of fused silica packed with a chromatographic stationary phase are used to clean the sample. For static nanospray, the goal is to introduce the sample by electrospray ionization at low flow rates (20-40 nanoliters/minute) from a small initial volume of sample (~1-5 µL) allowing extended MS analysis time. This is accomplished by placing the sample into a nanospray emitter which can be a pulled borosilicate glass tip coated with a conductive coating or from a "nozzle" in an array of microfabricated nozzles. ZipTips columns or other prepared microcolumns are currently used for removal of contaminants prior to mass spectrometric analysis.

One problem experienced by practitioners in the field in the application of ZipTips columns or microcolumns to the preparation of samples is poor recovery, particularly in the presence of buffers, detergents, salts, and chaotropes such as Tris, sodium dodecyl sulfate (SDS), urea, etc. For example, peptides extracted from one-dimensional or two-dimensional gels following in-gel digestion of separated proteins, wherein the gels contain around 0.1 percent of SDS, tend to have poor recovery using either ZipTips columns or microcolumns. Additionally, aspiration of samples through the packed bed of the ZipTips column often results in sample loss.

Moreover, the application of ZipTips pipette columns in concentrating a sample (>1.5 µL) is severely limited. The limitations articulated for ZipTips columns equally apply to microcolumn preparations. In order to effectuate the concentration of a sample using either ZipTips columns or a microcolumn, multiple steps of passing a sample through one of these devices must occur. As this reiteration occurs, progressively more sample can be lost resulting in poor recovery. Further, aspirating a sample through a ZipTips columns or microcolumn often results in air being introduced into the packing bed resulting in poor retention/recovery of the analytes of interest.

A further issue encountered by practitioners in this field is difficulty in manipulating microliter volumes through ZipTips columns or a microcolumn with the concomitant loss of sample.

Currently there is a need for a sample preparation device that effectively removes contaminants from the sample, concentrates the sample and permits easy manipulation of small volumes of liquid. The present invention addresses the aforementioned issues and provides a solution that effectively eliminates concerns present in the prior art.

SUMMARY

The present invention pertains to a sample preparation plate used to prepare a sample for mass spectrometric analysis. In particular, the instant invention pertains to a sample plate used to concentrate a sample as well as remove contaminants from the sample while providing easy manipulation of small liquid droplets on a surface with minimal sample loss.

In one embodiment, a sample plate for mass spectrometry analysis, comprising a platform is disclosed. In this embodiment, the platform is composed of a planar substrate. The substrate comprises regions of hydrophobicity and regions of hydrophilicity. The hydrophilic regions are target regions for receiving a liquid sample droplet.

In one embodiment, a sample plate for mass spectrometry analysis comprising a platform is disclosed. In this embodiment, the platform is composed of a substrate in which one or more wells are disposed therein. Each of these wells has a hydrophobic wall region and a hydrophilic basal region is disclosed. These wells are for receiving sample.

In another embodiment, a method of preparing a sample for mass spectrometric analysis is disclosed. This method involves providing a sample plate of the present invention. A liquid sample is then applied to a hydrophilic locus along a planar substrate comprising hydrophobic and hydrophilic regions. Alternatively, the liquid sample is applied to a well within the sample plate comprising a plurality of wells. The sample is then permitted to dry such that any residual sample material is concentrated within the hydrophobic well.

In one particular aspect of this embodiment, a droplet of solvent is added to a sample plate where solvent is added to the dried sample and is then transferred to a conductively-coated pulled-tip borosilicate glass capillary for static nanospray analysis.

In another particular aspect of this embodiment, a droplet of solvent is added to the dried sample residing on the sample plate. The liquid sample is then transferred onto a MALDI target plate. Once on the target plate, a MALDI matrix is then added in preparation for MALDI MS analysis. This also applies to cases where the UV absorbing molecule is covalently bonded to the surface and thus an integral part of the substrate. Alternatively, a DIOS (Direct Ionization On Silicon) procedure can be used where a porous or non-porous silicon substrate is the matrix.

In yet another aspect of this embodiment, a droplet of solvent is applied to the dried sample. Then the liquid sample is transferred to a sample vial for further analysis. Further analysis can include, but is not limited by subjecting the sample to LC/MS. Additionally, the sample can be subjected to nanospray, automated nanospray, MALDI and the like.

BRIEF DESCRIPTION OF THE DRAWINGS

FIG. 1 (a) is one embodiment of the present invention, (b) depicts an individual well;

DETAILED DESCRIPTION

Figure 2A:
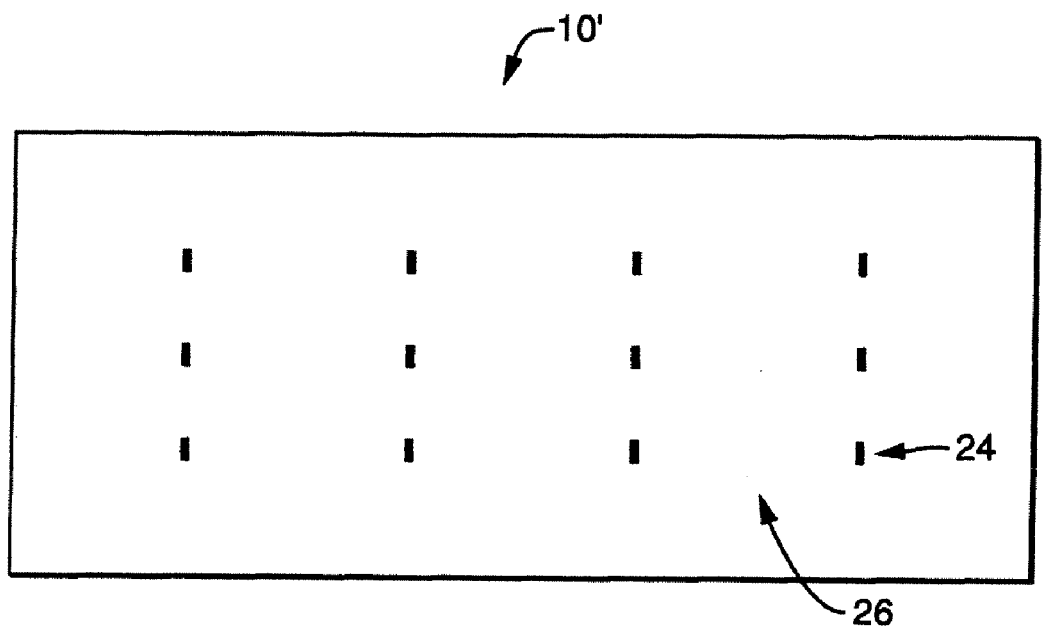
FIG. 2 is another embodiment wherein the substrate is a planar structure, (a) depicts one aspect of the present embodiment, and (b) is a side perspective of this embodiment.

The present invention pertains to a sample preparation plate used to prepare an analyte sample for mass spectrometric analysis. In particular, the instant invention pertains to a sample plate used to concentrate a sample containing one or more analytes as well as purifying a sample by removing contaminants while providing easy manipulation of small liquid droplets on a surface with minimal sample loss.

The sample of the present invention can comprise proteins, peptides, nucleic acids, and other small molecules of biological interest, such as drugs, drug metabolites, etc., that also bind to material contained in the hydrophilic well region. The sample can contain contaminants such as salt, urea, etc. that will be eliminated during sample preparation.

FIG. 1 illustrates one embodiment of the present invention. Unlike sample plates in the prior art, the sample plate 10 of the present invention has a platform 14 in which a plurality of wells 12 are defined therein. In one aspect of this embodiment, the platform 10 can be a ninety-six well microtiter plate. In another aspect, the platform 10 is a three hundred and eighty-four microtiter plate. The present invention embraces any microtiter plate configuration. It is desirable that each well has a volume capacity of from around 0.5 µL to around 100 µL. The wells in one embodiment are conical in shape with a hydrophilic base (basal region) and hydrophobic walls. The shape of the well need not be conical it could be circular, any geometric configuration is acceptable, what is important in this embodiment is that whatever the configuration, the platform needs to define wells that have a hydrophobic wall region and a hydrophilic basal region.

The substrate forming the platform 14 can be but is not limited to plastic, polyprolene, PTFE, Teflon, stainless steel, aluminum, glass, silicon, and alike. FIG. 1b is a depiction of an isolated well 12 with a liquid droplet 22 disposed therein. The wells 12 efficiently contain a liquid droplet 22 that is disposed within the well. The well 12 has a circumferential hydrophobic wall region 16. By hydrophobic it is meant a surface that is unwettable and liquid-repellant including those liquids that are organic in nature. This wall region 16 is comprised of hydrophobic material such as Teflon, PDMF and/or other hydrophobic substances known in the art. When a liquid droplet 22 is added to a well 12 having this hydrophobic wall region 16, there is a thermodynamic force of repulsion between the well region 16 of the well 12 and the surface of the liquid droplet. This repulsion promotes structural integrity of the aqueous droplet. The droplet 22 needs to be anchored into the well 12. This is accomplished by a hydrophilic region 18 that is comprised of hydrophilic materials such as polystyrene and/or other hydrophilic substances known in the art. The hydrophilic surface of the basal region 18 forms polar interactions with polar groups located on the surface of the droplet 22. These non-covalent interactions are sufficient to hold the droplet 22 in place within the well 12. By hydrophilic it is meant a surface that is wettable including using liquids other than aqueous liquids.

In one embodiment, the surface of a substrate can be coating using, for example, Teflon. The coating can be sprayed on or heat-shrink applied. The precise manner of application can be a method well known to those skilled in the art. The coated structure than can have a microfined or textured appearance.

Figure 2B:
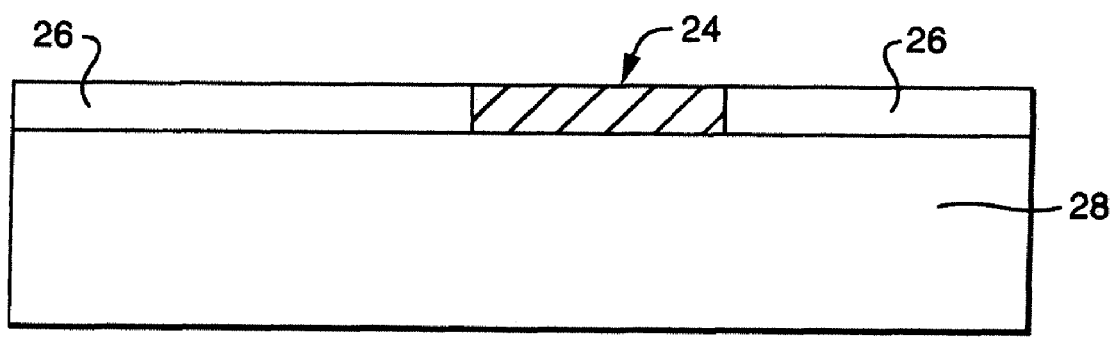

FIG. 2 illustrates another embodiment of the present invention. In this embodiment, the sample preparation plate is a planar surface. In one aspect of the present embodiment, one surface of the plate 10' comprises zones of hydrophilicity 24 and zones of hydrophobicity 26. See FIG. 2a. The hydrophobic zones (or regions) 26 can be comprised of a hydrophobic substance like Teflon. Other hydrophobic substances are also within the scope of this embodiment. Polystyrene, as well as other hydrophilic substances, can make up the hydrophilic zones 24 along a surface of the plate 10'. FIG. 2b depicts a side view of the sample plate 10'. In FIG. 2b the substrate 28 serves as the base for the plate 10'. On one surface of the substrate 28 lie the hydrophobic zones 26 and hydrophilic zones 24. The hydrophilic regions 24 serve to anchor an aqueous droplet of liquid containing a sample of one or more analytes, while the hydrophobic regions 26 promote the maintenance of the droplet structural integrity. The substrate 28 can be comprised of plastic, polymer, stainless steel, aluminum, glass, silicon, or alike. Optionally, walls (not shown) can be disposed about the perimeter of the sample plate 10'. The walls if present are typically composed of a hydrophobic substance such as Teflon. The alignment of the two regions at the surface does not have to be precise, the hydrophilic material can protrude slightly above the surrounding the hydrophobic region or the surface of the hydrophilic material can be located slightly below.

The present invention provides for the concentration of sample, removal of contaminants, and ease of manipulation of small liquids without the concomitant loss of sample. The sample is concentrated due to the surface tension of the sample droplet. As the solvent evaporates, the analytes are drawn to the hydrophilic region of the well. The analytes include, but are not limited to, proteins, peptides, small molecules of biological interest which can bind to the hydrophilic material. The analytes bind to the hydrophilic portion of the well. As the sample plate is washed, contaminants are removed while the analytes remain in tact. The samples disposed along the sample plate can be easily manipulated using, for example, a pipette. Given that there are no steps involving devices with packed beds in the present invention, loss of sample is minimized.

In one embodiment, a method of preparing a sample for mass spectrometric analysis is disclosed. A liquid droplet 22 putatively containing the sample of interest is deposited onto the sample plate 10 of the present invention. See FIG. 1. The sample plate 10 comprises one or more wells 12. Each well 12 defines a hydrophobic wall region 16 and a hydrophilic basal region 18. See FIG. 1b. The liquid droplet 22 is disposed within one or more wells 12. The sample is then allowed to dry within the well structure 12. The sample can be allowed to dry at ambient temperature and pressure, or elevated temperatures may be used to dry the sample that can range from about 30° C. to about 60° C. To assist in the drying process, the sample plate 10 containing the sample can be subjected to negative pressure using a vacuum apparatus. Heat can also be applied to the sample plate while a vacuum is applied. For example, if a sample preparation contains significant salt, then it may be advantageous to employ a vacuum so as to facilitate drying of the sample droplet. If the analytes decompose at elevated temperatures, application of a vacuum can assist in the removal of contaminants. The use of a vacuum allows for lower temperatures to be used for drying.

Alternatively, the sample plate 10' of the present invention is a surface, comprising a substrate 28 upon which zones of hydrophilicity 24 and hydrophobicity 26 reside. See FIG. 2. A liquid droplet containing an analyte sample of interest is deposited onto the sample plate 10', preferably onto one or more zones of hydrophilicity 24.

In operation, a sample plate, either one that contains wells or one that does not, is first pretreated with a solvent to clean the operational surface (i.e., the surface upon which sample is to be deposited). Typically, methanol or acetonitrile with around 0.1-1.0% formic acid (or ~0.1-1.0% trifluoroacetic acid, "TFA" or ~0.1-2.0% acetic acid) is used for pretreating the surface. The operational surface of the plate is then allowed to dry. The sample containing the analytes of interest is then deposited upon the operational surface of the plate either in a well or on a hydrophilic locus. The sample must have a pH of less than 4.0 and must be maintained throughout the process by adding volatile organic acids. The delivery solvent in which the sample is contained comprises, for example, around 0.1-1.0% formic acid or around 0.1-1.0% TFA or around 0.1-2.0% acetic acid with an organic component comprising up to around 30% of the solvent. Methanol or acetonitrile are but two examples of appropriate solvent to be employed in the delivery solvent. In the case of polystyrene or other hydrophilic binding materials, a modifier, such as a detergent (for example, 0.1% SDS) or denaturing agent (for example, urea) or chaotropic agents can be added to the delivery solvent to enhance binding of the desired analytes to the surface. Since this modifier will then be removed in the wash step, it will not affect the quality of the MS spectrum. The sample can be allowed to dry.

Next, a wash solvent can be used. This wash solvent comprises around 0.1-1.0% formic acid or around 0.1-1.0% TFA or around 0.1-2.0% acetic acid. Following the wash step, the sample can be extracted using an extraction solvent. An example of the extraction solvent is acetonitrile or methanol (~5-100%). A particular example of an extraction solvent is a solution comprising around 70% acetonitrile and around 0.1-10% formic acid.

Figure 3:
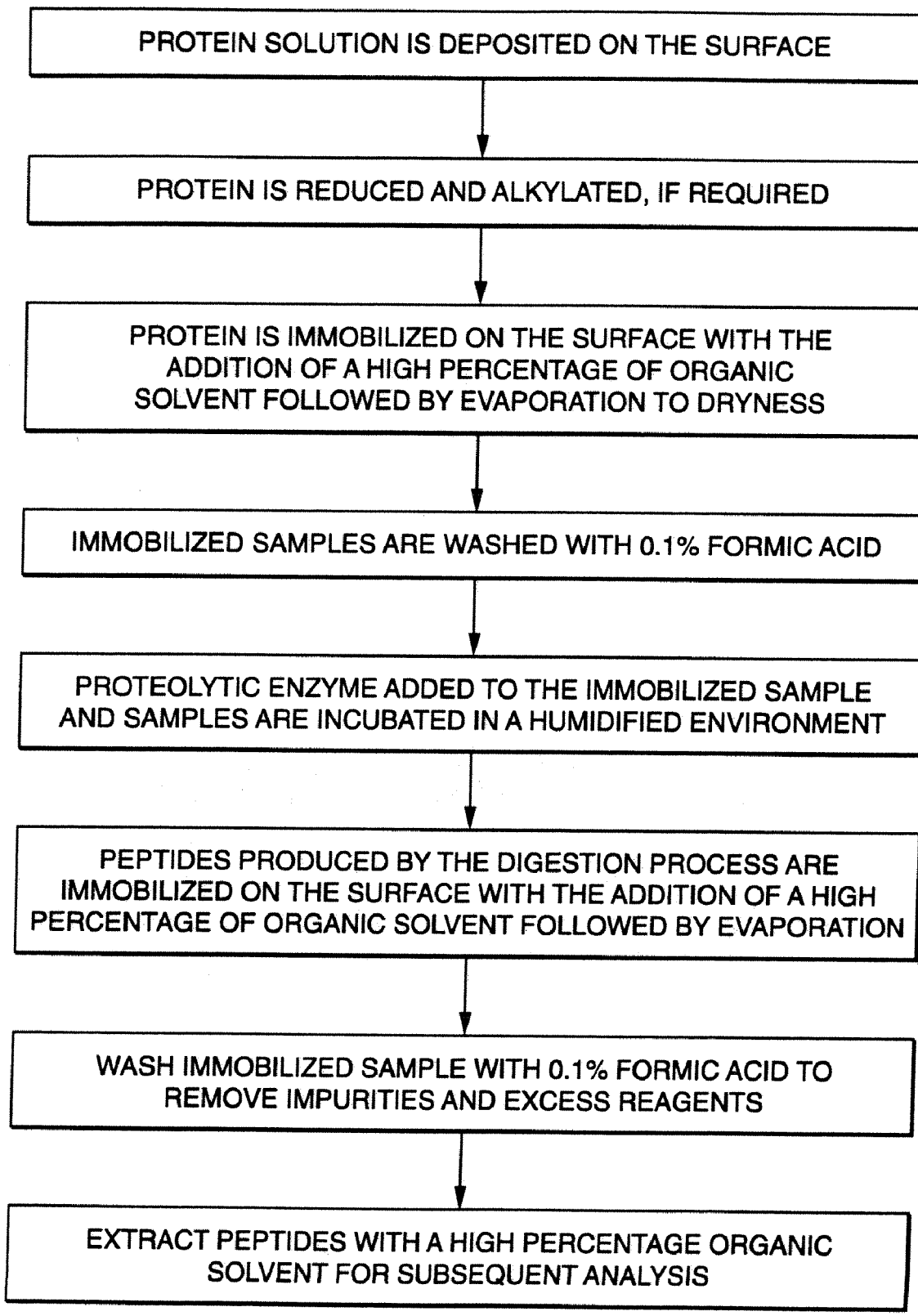
FIG. 3 is a flowchart illustrating one embodiment of the present invention.

As an illustrative example, FIG. 3 presents a flowchart for employing the present invention where the sample is a protein. Once bound, proteins can be immobilized thus allowing for a selective purification of the protein from a solution enabling in situ proteolytic digestion to be performed. One advantage of the present invention over traditional protein digestion approaches, for example, in-solution digests, is that all digestion steps including purification, concentration, reduction, alkylation and digestion are performed on the one surface. Further, reducing and alkylating agents, which can lead to inactivation of enzymes, are easily removed from the hydrophobic surface prior digestion. Additional advantages over traditional digest techniques include: minimal sample loss; protein dialysis is not required; selective removal of peptides following digestion and increased reaction rates with increased concentrations of reagents.

In FIG. 3, the sample containing a protein solution is deposited upon the surface of the sample preparation plate of the present invention. Some protein samples require either reduction or alkylation. This could proceed following placement of the sample on the sample plate. The addition of an organic solvent can assist in immobilizing the protein on the plate. Suitable organic solvents include, but are not limited to, acetonitrile, methanol, isopropyl alcohol or combinations thereof. The concentration of these solvents can range from 0.1% to 100%. The organic solvent will eventually evaporate. The immobilized protein can then be washed with, for example, 0.1% formic acid (or its equivalent). Following the wash, a proteolytic enzyme can be added to the immobilized sample under conditions suitable for proteolysis. This proteolytic step will produce smaller peptide samples from the parent protein. These peptide samples can then be immobilized on the plate by again subjecting the preparation to an organic solvent. The plate preparation can then be washed again using, for example, 0.1% formic acid. The peptide samples can then be extracted using a high percentage of an organic solvent and subjected to further analysis, for example, mass spectrometry. One skilled in the art will appreciate that variations can be applied to the above without deviating from the scope of the invention.

In one aspect of the present invention, a droplet of extraction solvent is added to the sample disposed within the well structure, or alternatively, within a hydrophilic zone of a planar sample plate. The extraction solvent comprises an organic component that can account for around 5-100% or greater of the overall solvent composition. Additionally, approximately 0.1-10% of the solvent is composed of an acid such as formic acid, or alike. Once the solvent has been added, the sample is then transferred to a conductively-coated pulled-tip borosilicate glass capillary for static nanospray analysis.

In another aspect, a droplet of solvent is added to the sample present in the well structure of the sample plate. Following the addition of solvent, the sample is transferred onto a MALDI target plate. Once on the MALDI target plate, an admixture is formed with the transferred sample using a MALDI matrix such as α-cyano-4-hydroxycinnamic acid. Now the sample is ready for MALDI analysis.

In yet another aspect, a droplet of solvent is added to the sample deposited within the well of the sample plate. The sample is then transferred to a sample vial for future analysis. For example, the sample can be used for LC/MS, MALDI, nanospray, etc.

Figure 4:
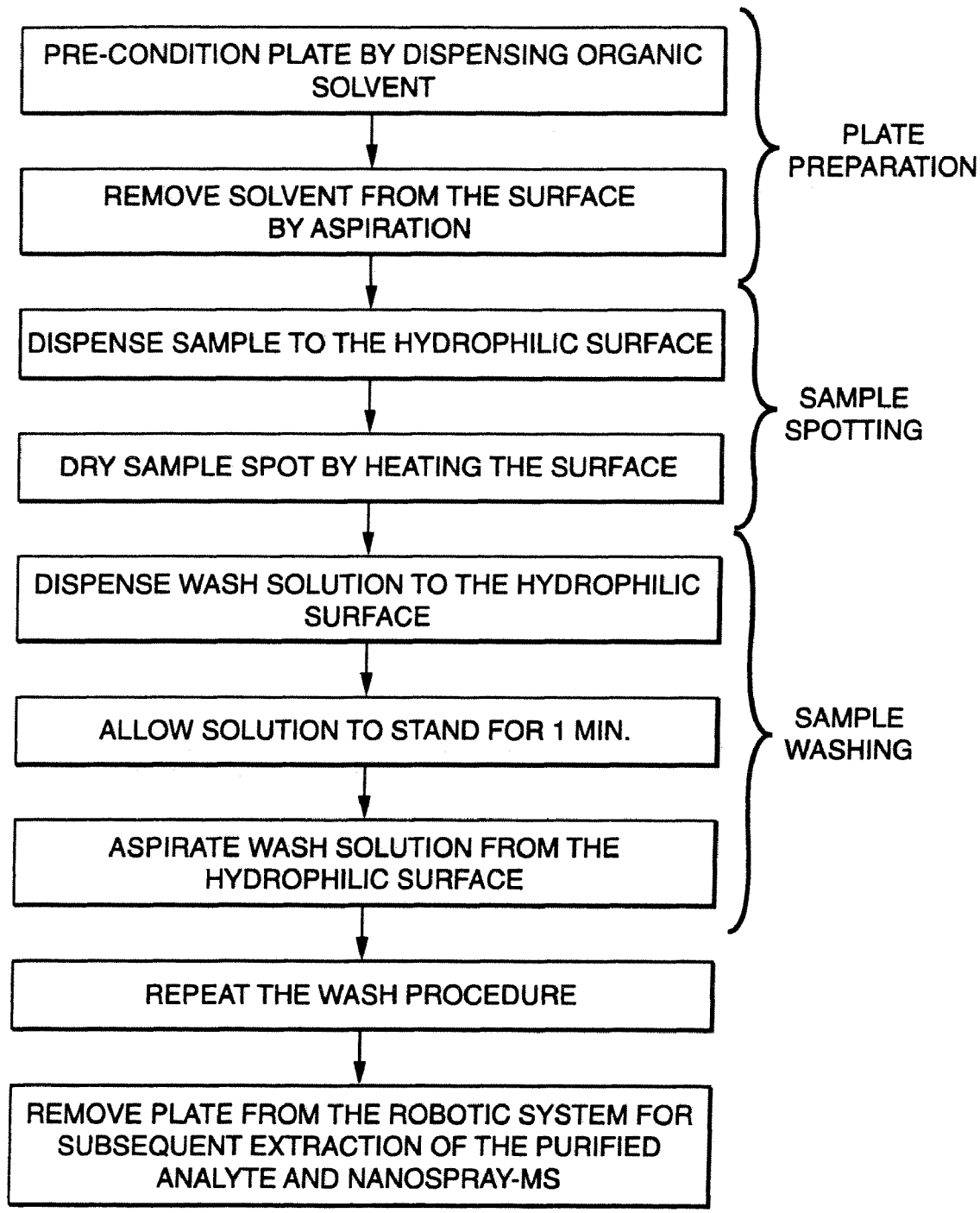
FIG. 4 is a flowchart illustrating one embodiment of the present invention that employs a robotic device.

The methods described herein can be accomplished using a suitable robotic device such as the Packard Multiprobe II from Perkin Elmer Life Sciences. FIG. 4 depicts one example of use for a robotic device in the present invention. As shown in FIG. 4, the process can be arbitrarily divided into three steps. The first step is the sample plate preparation. This step can comprise pre-conditioning the plate using an organic solvent followed by removing the solvent from the plate. Sample addition is the next step. The sample is added to the plate. In one aspect, the sample is added to a hydrophilic region of the plate. The sample can then be dried using, for example, elevated temperatures. The sample can then be subjected to a wash. In this step, the wash solution, for example, formic acid, is added to the plate-containing sample. The wash solution is allowed to stand for about one minute, however, one skilled in the art can determine what the optimal time should be without undue experimentation. Then, the wash solution is removed from the surface of the plate through, for example, aspiration. This wash procedure can be repeated and/or modified and remain within the scope of the invention. At this point, the plate can be removed from the robotic system for further processing and analysis.

EXAMPLE

Tryptic Digest of BSA

Figure 5:
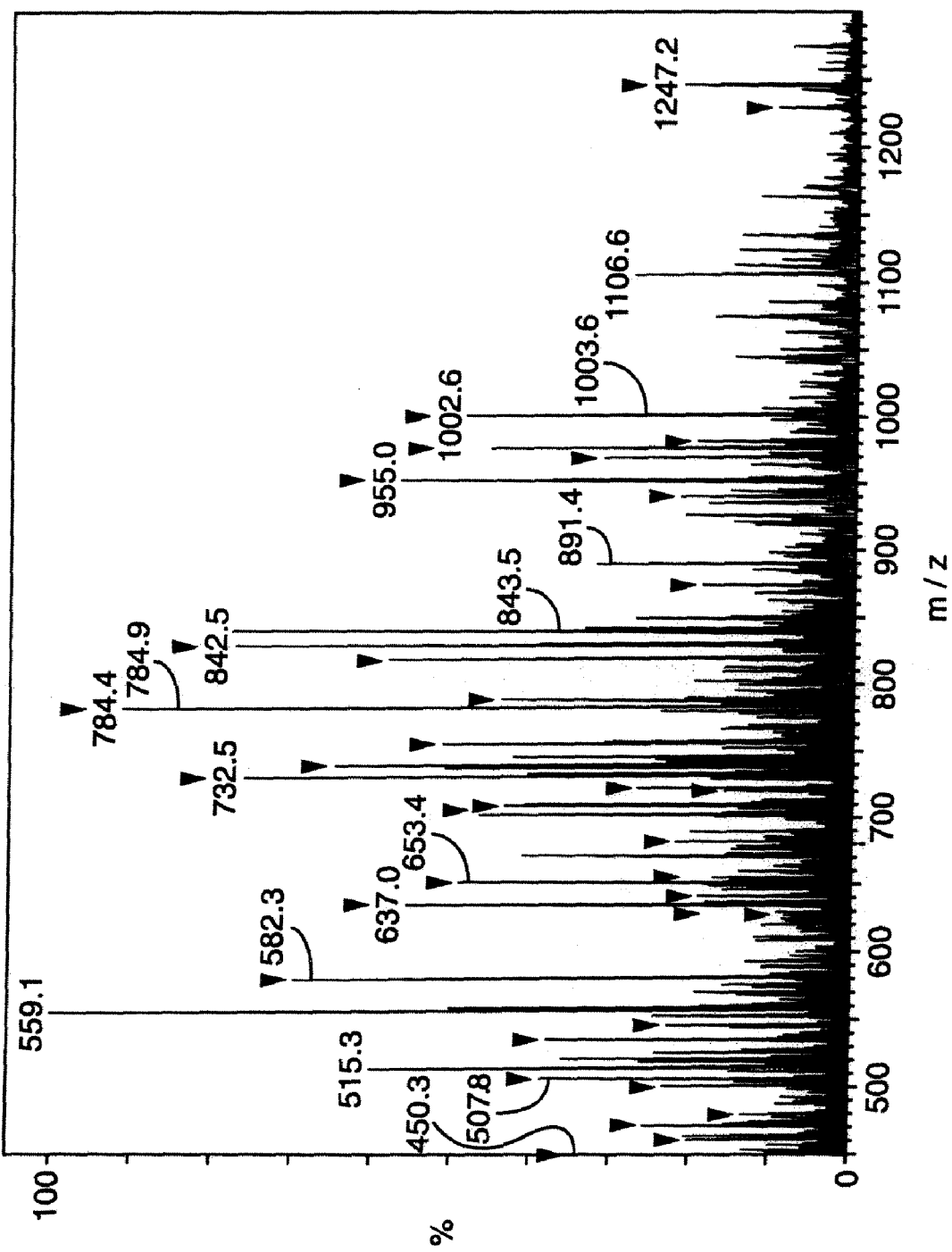
FIG. 5 is a nanospray mass spectrum of an in situ tryptic digestion of BSA performed using the sample plate of the present invention.

An example of the in situ tryptic digestion of 3 pmole of bovine serum albumin (BSA) followed by nanospray mass spectrometry of the digested peptides is shown in FIG. 5. Tryptic peptides of BSA are indicated with an arrow.

A sample of BSA (3 pmole) was deposited on a sample plate of the present invention. Following the deposition of BSA, the protein was reduced and alkylated with DTT (30 mM) and IAA (50 mM), respectively, and subsequently digested using trypsin (250 ng) for 5 hours. Digested peptides were washed with 0.1% formic acid and extracted with organic solvent prior to analysis. The extracted sample was then subjected to mass spectrometry. Samples were analyzed using a Q T of mass spectrometer equipped with a nanospray source. The capillary and cone voltages used were 900 and 40 volts respectively. Cone gas flow rate was 50 L/hr.

While this invention has been particularly shown and described with references to specific embodiments, it will be understood by those skilled in the art that various changes in form and details may be made therein without departing from the spirit and scope of the invention as defined by the appended claims.

What is claimed is:

1. A device for the presentation of samples for mass spectrometry analysis comprising:
   a substrate, said substrate forming a platform and one or more wells for receiving a fluid sample, said one or more wells having a wall region and a basal region,
   wherein said wall region is hydrophobic and said basal region is hydrophilic.

2. The device of claim 1 where said one or more wells are conical.

3. The device of claim 1 where said wall region is comprised of a material selected from the group consisting of PTFE, polydimethylsiloxane.

4. The device of claim 1 where said basal region is comprised of material selected from the group consisting of polystyrene.

5. The device of claim 1 where said substrate is comprised of material selected from the group consisting of plastic, PTFE, polypropylene, plastic, stainless steel, aluminium, glass, silicon.

6. A method of preparing a sample for mass spectrometric analysis comprising the steps of:
   providing a substrate, said substrate forming a platform and one or more wells for receiving a fluid sample, said one or more wells having a wall region and a basal region, where said wall region is hydrophobic and said basal region is hydrophilic;
   applying a liquid sample material to a well within said sample plate; and,
   drying said sample such that residual sample material is concentrated within said well.

7. The method of claim 6 further comprising the steps of:
   applying a droplet of solvent to said sample to make a second sample solution, and,
   transferring at least some of said second sample solution to a conductively-coated pulled-tip borosilicate glass capillary or a microfabricated nozzle for static nanospray MS analysis.

8. The method of claim 7 wherein said solvent comprises an organic component and an acid component, wherein said organic component accounts for about 40% or greater of said solvent, wherein said acid component is between about 0.1-10% of said solvent and wherein the remainder component is water.

9. The method of claim 6 further comprising the steps of:
   applying a droplet of solvent to said sample to make a second sample solution, transferring at least some of said sample of said second sample solution onto a MALDI target plate; and
   forming an admixture of at least some of said second sample solution with a MALDI matrix for MALDI MS analysis.

10. The method of claim 9 wherein said solvent comprises an organic component and an acid component, wherein said organic component accounts for about 40% or greater of said solvent, wherein said acid component is between about 0.1-10% of said solvent and wherein the remainder component is water.

11. The method of claim 6 further comprising the steps of:
    applying a droplet of solvent to said sample to make a second sample solution, and,
    transferring at least some of said second sample solution to a sample vial.

12. The method of claim 11 wherein said solvent comprises an organic component and an acid component, wherein said organic component accounts for about 40% or greater of said solvent, wherein said acid component is between about 0.1-10% of said solvent and wherein the remainder component is water.

* * * * *